(12) United States Patent
Gilad-Bachrach et al.

(10) Patent No.: US 9,331,743 B2
(45) Date of Patent: May 3, 2016

(54) BIOLOGICAL ENTITY COMMUNICATION CHANNEL

(75) Inventors: Ran Gilad-Bachrach, Bellevue, WA (US); Gerald R. DeJean, Redmond, WA (US); Trang Thuy Thai, Atlanta, GA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 280 days.

(21) Appl. No.: 13/314,635

(22) Filed: Dec. 8, 2011

(65) Prior Publication Data

US 2013/0149965 A1 Jun. 13, 2013

(51) Int. Cl.
*H04B 5/00* (2006.01)
*H04B 7/00* (2006.01)

(52) U.S. Cl.
CPC ........................................ *H04B 5/00* (2013.01)

(58) Field of Classification Search
CPC ........................................................ H04B 5/00
USPC ...................................... 455/41.1, 41.2, 41.3
See application file for complete search history.

(56) References Cited

U.S. PATENT DOCUMENTS

| | | | |
|---|---|---|---|
| 6,223,018 B1* | 4/2001 | Fukumoto et al. | 455/41.1 |
| 6,888,502 B2 | 5/2005 | Beigel et al. | |
| 2010/0105323 A1* | 4/2010 | Kawano et al. | 455/41.1 |
| 2010/0238955 A1* | 9/2010 | Sung et al. | 370/498 |
| 2010/0246643 A1* | 9/2010 | Lim et al. | 375/147 |
| 2010/0330910 A1* | 12/2010 | Yan et al. | 455/41.2 |
| 2011/0082523 A1* | 4/2011 | Nghiem et al. | 607/60 |
| 2011/0118030 A1* | 5/2011 | Walley et al. | 463/37 |
| 2011/0148652 A1* | 6/2011 | Kim et al. | 340/691.1 |

OTHER PUBLICATIONS

Hwang, et al., "Analysis of Signal Interference in Human Body Communication Using Human Body as Transmission Medium", Retrieved at <<http://research.microsoft.com/en-us/um/people/shliu/cao_infovis10.pdf>>, International Symposium on Antennas and Propagation Society (IEEE), Jul. 9-14, 2006, pp. 495-498.
Conway, et al., "Low-Profile Patch Antenna for Over-Body Surface Communication at 2.45 GH", Retrieved at <<http://ieeexplore.ieee.org/stamp/stamp.jsp?tp=&arnumber=4227479>>, International workshop on Antenna Technology: Small and Smart Antennas Metamaterials and Applications (IWAT), Mar. 21-23, 2007, pp. 416-419.

(Continued)

*Primary Examiner* — Ping Hsieh
*Assistant Examiner* — Xin Jia
(74) *Attorney, Agent, or Firm* — Alin Corie; Sandy Swain; Micky Minhas

(57) ABSTRACT

Biological entity communication channel techniques are described. In one or more implementations, an apparatus includes a signal conductor having a side that is configured to be disposed proximal to a surface of a biological entity to use at least a part of the biological entity as a transmission channel to transmit a signal received by the signal conductor from an electrical device. The apparatus also includes a ground layer configured to be disposed on an opposing side of the signal conductor from the side of the signal conductor that is configured to be disposed against the surface of the biological entity.

14 Claims, 6 Drawing Sheets

(56) References Cited

OTHER PUBLICATIONS

Zhu, et al., "High Speed Intra-Body Communication for Personal Health Care", Retrieved at <<http://ihome.ust.hk/~zhuhongjie/publications/Zhu%20-%20High%20Speed%20Intra-Body%20Communication%20for%20Personal%20Health%20Care.pdf>>, Proceedings of the 31st IEEE International Conference on Engineering in Medicine and Biology Society (EMBC), Sep. 2-6, 2009, pp. 709-712.

Hall, et al., "Antennas and Propagation for Body Centric Communications", Retrieved at <<http://www.mwjournal.com/BGDownload/bodycentric.pdf>>, Proceedings of the IEEE First European Conference on Antennas and Propagation (EuCAP), Nov. 6-10, 2006, pp. 1-7.

Franklin, et al., "Personal Area Network for Biomedical Monitoring Systems Using Human Body as a Transmission Medium", Retrieved at <<http://www.sersc.org/journals/IJBSBT/vol2_no2/3.pdf>>, International Journal of Bio-Science and Bio-Technology, vol. 2, No. 2, Jun. 2010, pp. 23-28.

Yoo, et al., "Low Energy Wearable Body-Sensor-Network", Retrieved at <<http://ieeexplore.ieee.org/stamp/stamp.jsp?arnumber=05333156>>, Proceedings of the 31st IEEE annual International Conference on Engineering in Medicine and Biology Society, Sep. 2-6, 2009, pp. 3209-3212.

T.G. Zimmerman; "Personal Area Networks: Near-field intrabody communication"; IBM Systems Journal, vol. 35, Nos. 3&4pp. 609-617Published 1996.†

\* cited by examiner
† cited by third party

BIOLOGICAL ENTITY COMMUNICATION CHANNEL

BACKGROUND

Users may utilize a variety of different data in a given day that may be sensitive to the user. For example, a user may use purchase credentials such as a credit card number and expiration date to purchase goods or services. A user may also utilize login information to access a user account, gain access to a physical location (e.g., a vehicle or building), and so on.

Consequently, exposure of this data may make the data susceptible to compromise by a malicious party. For example, holding a credit card may enable a person to quickly read enough information that is sufficient to make a purchase, thereby compromising the user's account. Although techniques were developed to reduce exposure of this data, these conventional techniques could still be compromised by malicious parties and therefore were generally not adopted for use in public settings.

SUMMARY

Biological entity communication channel techniques are described. In one or more implementations, an apparatus includes a signal conductor having a side that is configured to be disposed proximal to a surface of a biological entity to use at least a part of the biological entity as a transmission channel to transmit a signal received by the signal conductor from an electrical device. The apparatus also includes a ground layer configured to be disposed on an opposing side of the signal conductor from the side of the signal conductor that is configured to be disposed against the surface of the biological entity.

In one or more implementations, an apparatus is disposed proximal to a surface of a human body to form a coaxial communication channel, using at least a part of the human body that is suitable to communicate a signal from an electrical device. The signal is transmitted using the part of the human body that forms the coaxial communication channel.

In one or more implementations, an apparatus includes a ground layer and a signal conductor configured to be disposed between the ground layer and a surface of a human body to use at least a part of the human body to serve as a coaxial transmission channel to transmit data received by the signal conductor from an electrical device as a guided wave signal to be communicated to another electrical device via the coaxial transmission channel.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different instances in the description and the figures may indicate similar or identical items.

DETAILED DESCRIPTION

Overview

Use of confidential data may be limited by an ability of malicious parties and others to compromise the data. Although techniques were developed to help secure communication from a user, these conventional techniques relied on generation of a quasi-static electrical field (e.g., a low frequency electrical field may behave like a static field in the operating distance based on which the detection is performed) that could be detected at a significant distance from the user. Therefore, data communicated using these conventional techniques could still be compromised by malicious parties and thus further complicate the management of the data.

Biological entity communication channel techniques are described. In one or more implementations, a secure communications channel is established by using at least part of a biological entity (e.g., a human body part such as an arm) as a transmission channel. Additionally, the techniques described herein may enable this transmission channel to be secure such that it is not significantly radiated "out" from the human body, e.g., less than eight millimeters. This may be done by forming a guided wave for transmission through a user's arm such that transmission channel acts as a coaxial channel, which may be performed by forming a ground layer over a signal conductor that is configured to contact a user's skin. Thus, a variety of sensitive data may be communicated through this channel (e.g., to another user via a handshake) thus reducing an ability of malicious parties to compromise this data. Further discussion of these techniques may be found in relation to the following sections.

In the following discussion, a variety of example implementations of a device and a biological entity are described. Additionally, a variety of different functionality that may be employed by the devices leveraging the communication channel are described for each example, which may be implemented in that example as well as in other described examples. Accordingly, example implementations are illustrated of a few of a variety of contemplated implementations as further discussion below.

Example Implementations

Figure 1:
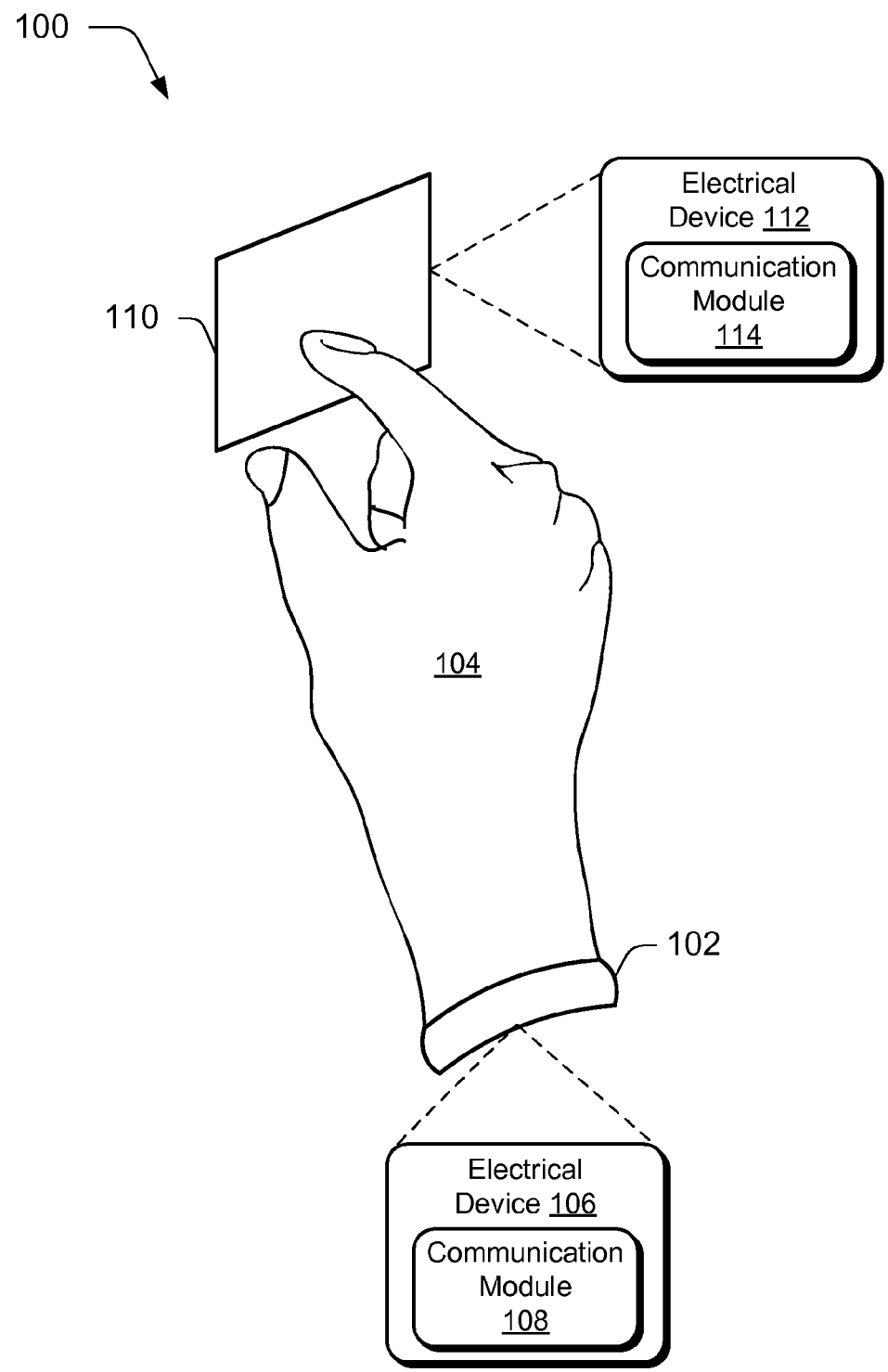
FIG. 1 is an illustration of an example implementation of an environment that is operable to employ biological entity communication techniques described herein.

FIG. 1 is an illustration of an example implementation of an environment 100 that is operable to employ the techniques described herein. The environment includes an apparatus 102 that in this example is configured to be wearable on a body, such as on an arm 104 of a human body. Other configurations of the apparatus 102 are also contemplated, such as part of another device such as a surface of a mobile communications device (e.g., a mobile phone or tablet), part of a user's wallet, jewelry that is wearable by the user, and so on.

Although the current example of FIG. 1 involves a human body, a variety of different biological entities may be contacted by the apparatus 102, e.g., the apparatus 102 may be formed to be wearable by a pet (e.g., dog, cat, bird), used in laboratory testing, or may involve a variety of different organisms.

The apparatus 102 is illustrated as being communicatively coupled to an electrical device 106. In one example, the electrical device 106 is configured as part of the apparatus 102 itself as illustrated, e.g., formed as an integral part of the apparatus 102. In another example, the electrical device 106 may be formed as a separate entity that is in communication with the apparatus 102, e.g., wired or wireless communication, to send and/or receive data.

The electrical device 106 may be configured in a variety of ways. For example, the electrical device 106 may employ a communication module 108 that may be configured to communicate data to the apparatus 102, which may then be sent by the apparatus using a biological entity such as the arm 104 of the human body as illustrated. In one example, the electrical device 106 is configured as computing device, such as a desktop computer, a mobile station, an entertainment appliance, a set-top box communicatively coupled to a display device, a wireless phone, a game console, a game controller, a remote control, and so forth. Thus, the electrical device 106 may range from full resource devices with substantial resources (e.g., personal computers, game consoles, tables, mobile communication devices) to a low-resource device with limited resources (e.g., game controllers, remote controls, medical sensors). A variety of other examples are also contemplated.

The apparatus 102 and the electrical device 106 may be configured to use a portion of a biological entity (e.g., the arm 104 of a human body in the illustrated example) as a communication channel to communicate a signal to another device. For example, a finger of the arm 104 of the human body is illustrated as contacting a surface 110 associated with another electrical device 112. The other electrical device 112 is illustrated as including a communication module 114 that is representative of functionality of the device to communicate using the surface 110. The surface 110 and the electrical device 112 may also be configured in a variety of ways. For example, the surface 110 may be part of the electrical device 112 that is configured to receive data to perform an action, such as credentials to facilitate a purchase of a good or service.

In another example, the surface 110 and the electrical device 112 may involve a similar configuration to that of the apparatus 102 and electrical device 106. The hand of the user's arm 104, for instance, may be used to "shake hands" with another user such that the users are in physical contact with each other. This contact may be used as a channel to communicate a signal between the electrical devices 106, 112 by using respective parts of the user's arms as a communication channel. The signal may be used to carry a variety of data, such as contact information, messages, user credentials (e.g., login information, purchase information), and so forth.

Regardless of a destination for the transmitted signal, the apparatus 102 may be employed to form a secure communication channel using a part of the biological entity, e.g., the user's arm 104. In one or more implementations, this communication is performed without substantially radiating the signal "outside" of the human body. Further discussion of an example configuration of the apparatus 102 that may be used to initiate such a signal may be found beginning in relation to FIG. 2.

Generally, functions described herein may also be implemented using software, firmware, hardware (e.g., fixed logic circuitry), or a combination of these implementations. The terms "module," "functionality," and "engine" as used herein generally represent software, firmware, hardware, or a combination thereof. In the case of a software implementation, the module, functionality, or engine represents program code that performs specified tasks when executed on a processor (e.g., CPU or CPUs) and is storable in one or more computer readable storage devices and thus is implementable at least partially in hardware. The features of the techniques described below are platform-independent, meaning that the techniques may be implemented on a variety of commercial computing platforms having a variety of processors.

For example, a computing device may also include an entity (e.g., software) that causes hardware of the computing device to perform operations, e.g., processors, functional blocks, and so on. For example, the computing device may include a computer-readable medium that may be configured to maintain instructions that cause the computing device, and more particularly hardware of the computing device to perform operations. Thus, the instructions function to configure the hardware to perform the operations and in this way result in transformation of the hardware to perform functions. The instructions may be provided by the computer-readable medium to the computing device through a variety of different configurations.

One such configuration of a computer-readable medium is a signal bearing medium and thus is configured to transmit the instructions (e.g., as a carrier wave) to the hardware of the computing device, such as via a network. The computer-readable medium may also be configured as a computer-readable storage medium and thus is not a signal bearing medium. Examples of a computer-readable storage medium include a random-access memory (RAM), read-only memory (ROM), an optical disc, flash memory, hard disk memory, and other memory devices that may use magnetic, optical, and other techniques to store instructions and other data.

Figure 2:
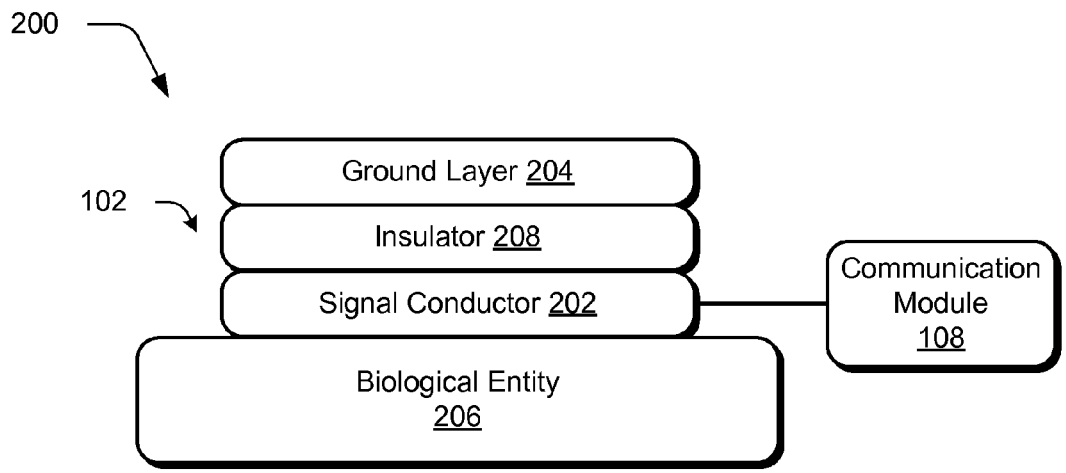
FIG. 2 depicts an example implementation showing an apparatus of FIG. 1 that is usable to implement a biological entity communication channel in greater detail.

FIG. 2 depicts an example implementation 200 showing the apparatus 102 of FIG. 1 that is usable to implement a biological entity communication channel in greater detail. The apparatus 102 is illustrated as including a signal conductor 202 and a ground layer 204 in contact with a biological entity 206. The ground layer 204 and the signal conductor 202 are separated, such as through use of an insulator 208, e.g., a substrate or other medium although other examples are also contemplated. The signal conductor 202 is illustrated as being coupled to a communication module 108 which may serve as a signal source to communicate a signal as well as a signal destination to which the signal conductor 202 is to pass a received signal, e.g., from a biological entity 206. Although the signal conductor 202 is shown in direct contact with the biological entity 206, a variety of other examples are also contemplated. For example, one or more additional conductors may be positioned between the signal conductor 202 and the biological entity which are configured to permit a signal to pass from the signal conductor 202 to the biological entity 206, e.g., through the use of one or more perforations.

Through positioning of the signal conductor 202 between the ground layer 204 and the biological entity, the apparatus 102 may establish a deliberate and secure communications channel on the biological entity 206 by forming a "biological" transmission channel through the biological entity 206. As previously described, this may include communication from a single user to another device, between users that are each wearing an electrical device configured to support such a channel (e.g., through a handshake and other contact), and so forth.

The signal conductor 202 may be formed from a variety of different conductive materials, such as a micro-strip line configured to cause fringing electromagnetic fields to be transferred into at least a portion of the biological entity 206, such as an arm of a human body. Through placement of the ground layer 204 on an opposing side of the signal conductor 202 from the biological entity 206, the apparatus 102 may implement a coaxial channel to cause a guided wave to be communicated through the biological entity 206, an example of which is further described in relation to the following figure.

Figure 3:
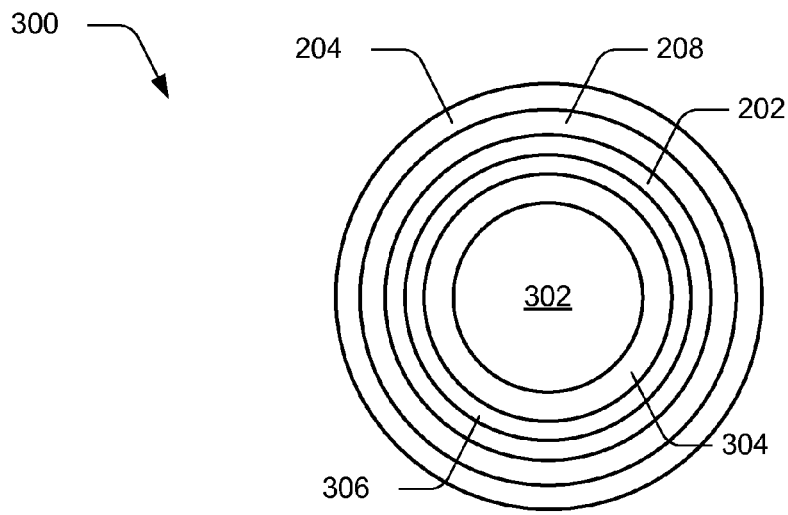
FIG. 3 depicts an example implementation showing a cross-sectional view of the apparatus and biological entity of FIG. 2 in greater detail as forming a coaxial channel usable to form and communicate a guided wave through the biological entity.

FIG. 3 depicts an example implementation 300 showing a cross-sectional view of the apparatus 102 and biological entity 206 of FIG. 2 in greater detail as providing a coaxial channel usable to form and communicate a guided wave through the biological entity 206. The biological entity 206 in this example is represented through layers of muscle 302, fat 304, and skin 306 as may be found in an arm 104 of a human body although other examples are also contemplated.

A signal conductor 202 is illustrated as disposed proximal to the skin 306 and thus a surface of the biological entity 206. The ground layer 204 is illustrated as disposed on an opposing side of the signal conductor 202 from the skin 306 and separated from the signal conductor 202 by the insulator 208.

This may be used to implement a "coaxial" arrangement of the apparatus 102 with the biological entity 206 to support transmission of a modified guided wave using the biological entity 206. Although the transmission is not exactly in the same form as that of a conventional coaxial transmission line, the transmission is closely bound to the open biological entity 206 acting as the inner conductor of a modified coaxial transmission line. Further, leakage of the signal from the signal conductor 202 is reduced and even substantially limited through this arrangement.

Therefore, depending on the choice of insulator 208 and the diameter of the ground layer 204, signals can be generated in two distinct bands. Signals in one band may be tightly bound to the open biological entity 206, and signals in another band may be unbound to the open biological entity 206 and radiated into space. For example, at a signal frequency of 400 MHz, the signal communicated through the skin 306 and signal conductor 202 is substantially undetectable at a distance greater than eight millimeters because the signal is bounded to the open biological entity 206. In another example, a signal at 1.5 GHz is detectable at distances much greater than eight millimeters. Therefore, the two forms of communication can operate simultaneously on the same device.

Conventional techniques, however, relied on at least two electrodes which contacted a body to form a static electrical field that was detectable at distances orders of magnitude greater and at lower bandwidths (e.g., five centimeters at ten MHz) than the distances and bandwidths at which the techniques described herein are detectable, e.g., eight millimeters at 400 MHz. Thus, the quasi-static electrical fields generated by these conventional techniques could become compromised and thus ill-suited for purposes in which security of data transmitted by the signal is desired.

Additionally, as is apparent from the previous example the bandwidth of a signal supported by the techniques described herein is significantly improved, such as from ten MHz of conventional techniques to four hundred MHz and greater (e.g., 1.5 GHz) using the techniques described herein. In one or more implementations, security (e.g., which increases at lower frequencies due to decreased leakage) and bandwidth (e.g., which increases at higher frequencies) may be adjusted as desired. These factors may also be controlled in a variety of other ways, such as through adjustment of the signal conductor 202 (e.g., for increased ability to cause the biological entity 206 to communicate a signal), the choice of insulator 208, and/or the adjustment of the ground layer 204, e.g., to provide increased shielding.

Figure 4:
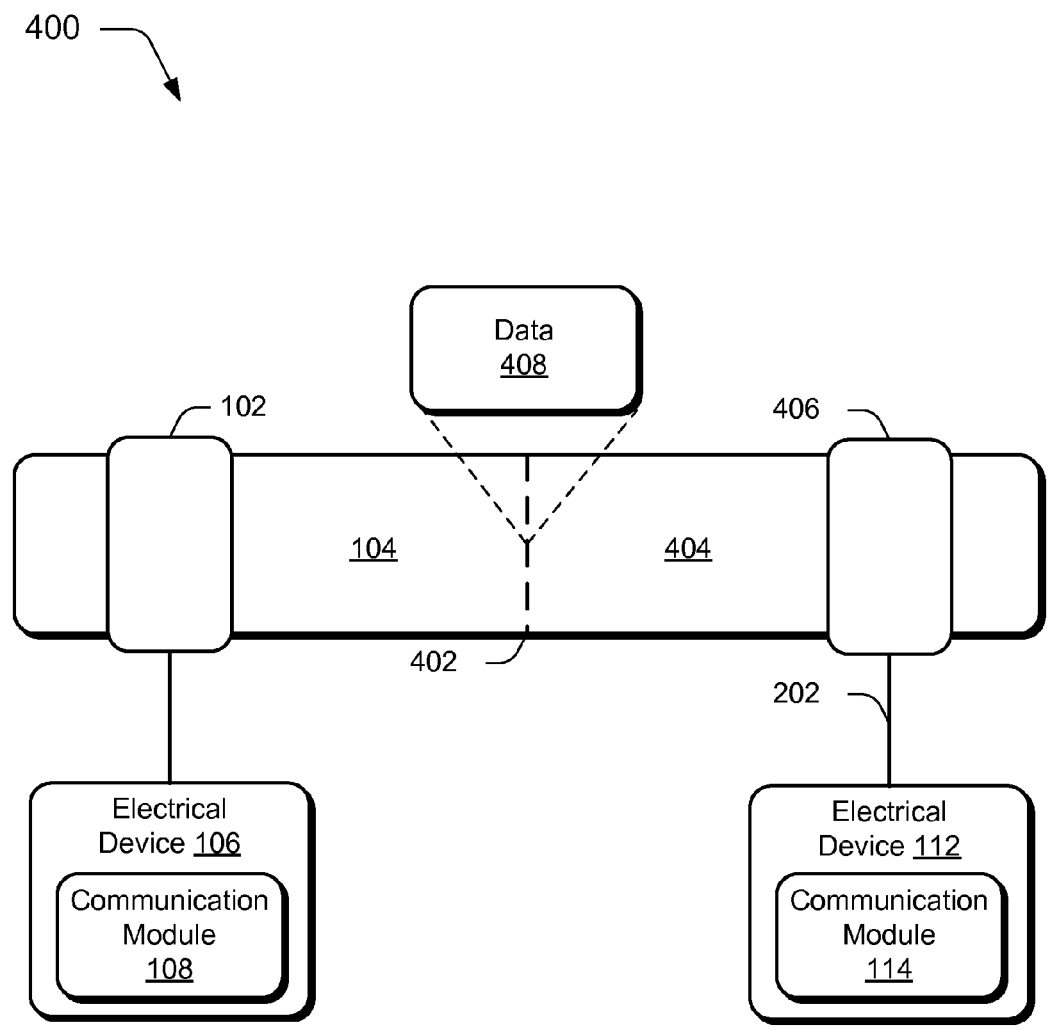
FIG. 4 depicts a system in an example implementation in which a communication channel is used to communicate data between two electrical devices using the techniques described herein

FIG. 4 depicts a system 400 in an example implementation in which a communication channel is used to communicate data between two electrical devices securely using the techniques described herein. In this example, the apparatus 102 is configured as a cuff that is disposed proximal to an arm 104 of a user. The apparatus 102 is also communicatively coupled to a communication module 108 of an electrical device 106.

The arm 104 of the user is in physical contact 402 with a body 404 of another user in this example, such as in an instance in which the users shake hands or otherwise. The body 404 of the other user also includes an apparatus 406 that is configured to form a biological communication channel through at least a part of the user as described for apparatus 102. Apparatus 406 is also communicatively coupled to a communication module 114 of an electrical device 112 as described previously in relation to FIG. 4.

Thus, in this example, the electrical devices 106, 112 may leverage corresponding apparatuses 102, 406 to use at least part of the respective user's bodies to communicate data 408, one with another. As previously described, an ability to detect the data transmitted through the signal channel tightly bound to the open biological entity 206 may be minimal unless contact with one of the users is achieved and thus a relatively high level of security may be achieved.

A variety of different data 408 may be communicated between the electrical devices 106, 112. For example, the data 408 may be configured to identify a user, such as to access a premises, a vehicle (e.g., upon grasping a handle of a car door or other surface of the car), transmit credentials usable to purchase a good or service, identify a user for a purchase loyalty program, login a user to a computing device, used for medical sensing (to detect a temperature of another user), and so on. A variety of other examples are also contemplated, further discussion of which may be found in relation to the following procedure.

Figure 6:
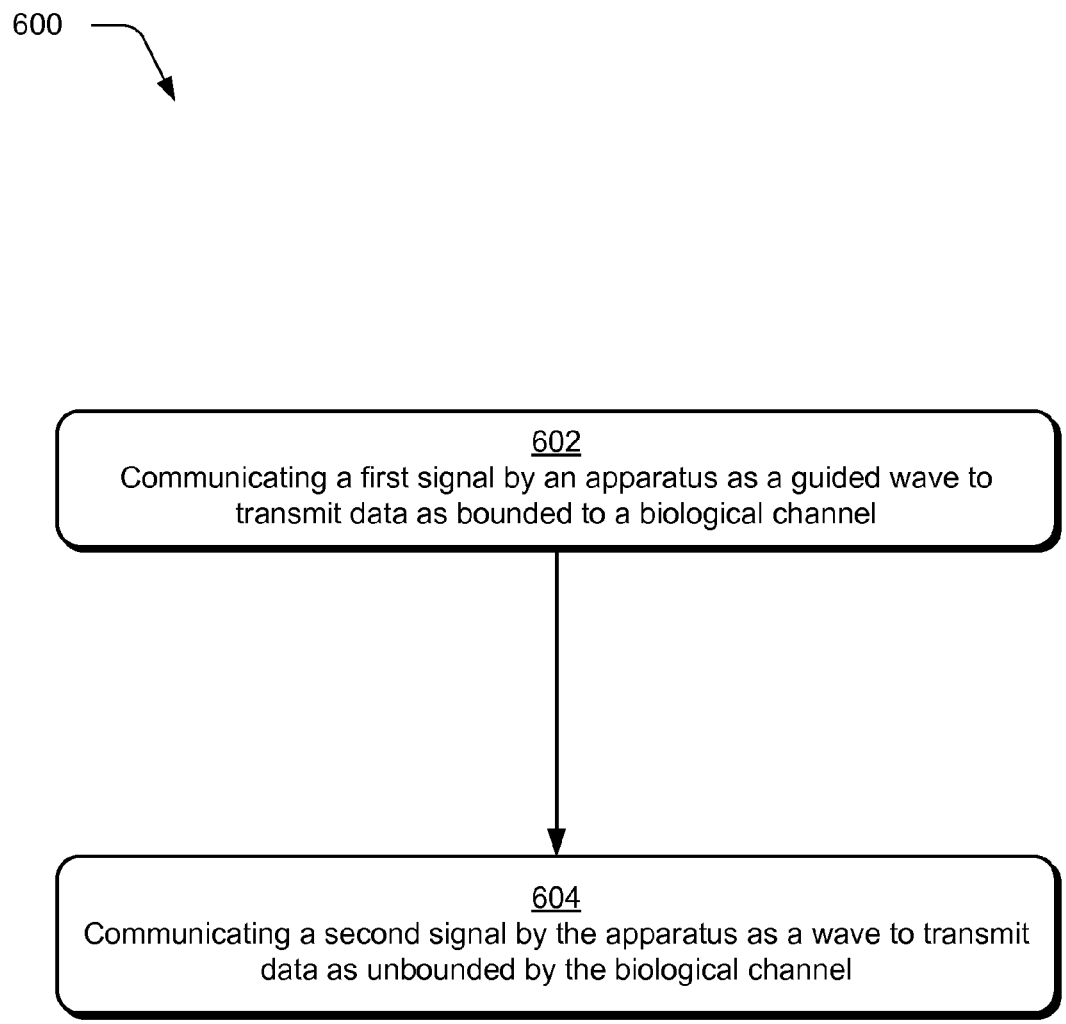
FIG. 6 depicts a procedure in an example implementation in which communication of first and second signals is performed to support communication that is both bounded and unbounded by a biological channel.

A variety of different data may be communicated between the electrical devices 106 or 112 with a third device located remotely (e.g. few meters away) at a different frequency band (e.g. 1.5 GHz) using the unbounded channel for variety of purposes including but not limited to connecting using one or more wireless communication standards, e.g., to connect to local or world wide web networks in the platforms including but not limited to IEEE 802.11 (i.e., Wi-Fi), IEEE 802.16 (Wi-MAX), Bluetooth, near field communication, and so forth, further discussion of this may be found in relation to FIG. 6.

Example Procedure

The following discussion describes biological entity communication channel techniques that may be implemented utilizing the previously described systems and devices. Aspects of each of the procedures may be implemented in hardware, firmware, software, or a combination thereof. The procedures are shown as a set of blocks that specify operations performed by one or more devices and are not necessarily limited to the orders shown for performing the operations by the respective blocks. In portions of the following discussion, reference will be made to the environment 100, example implementations 200-300, and system 400 of FIGS. 2-4, respectively.

Figure 5:
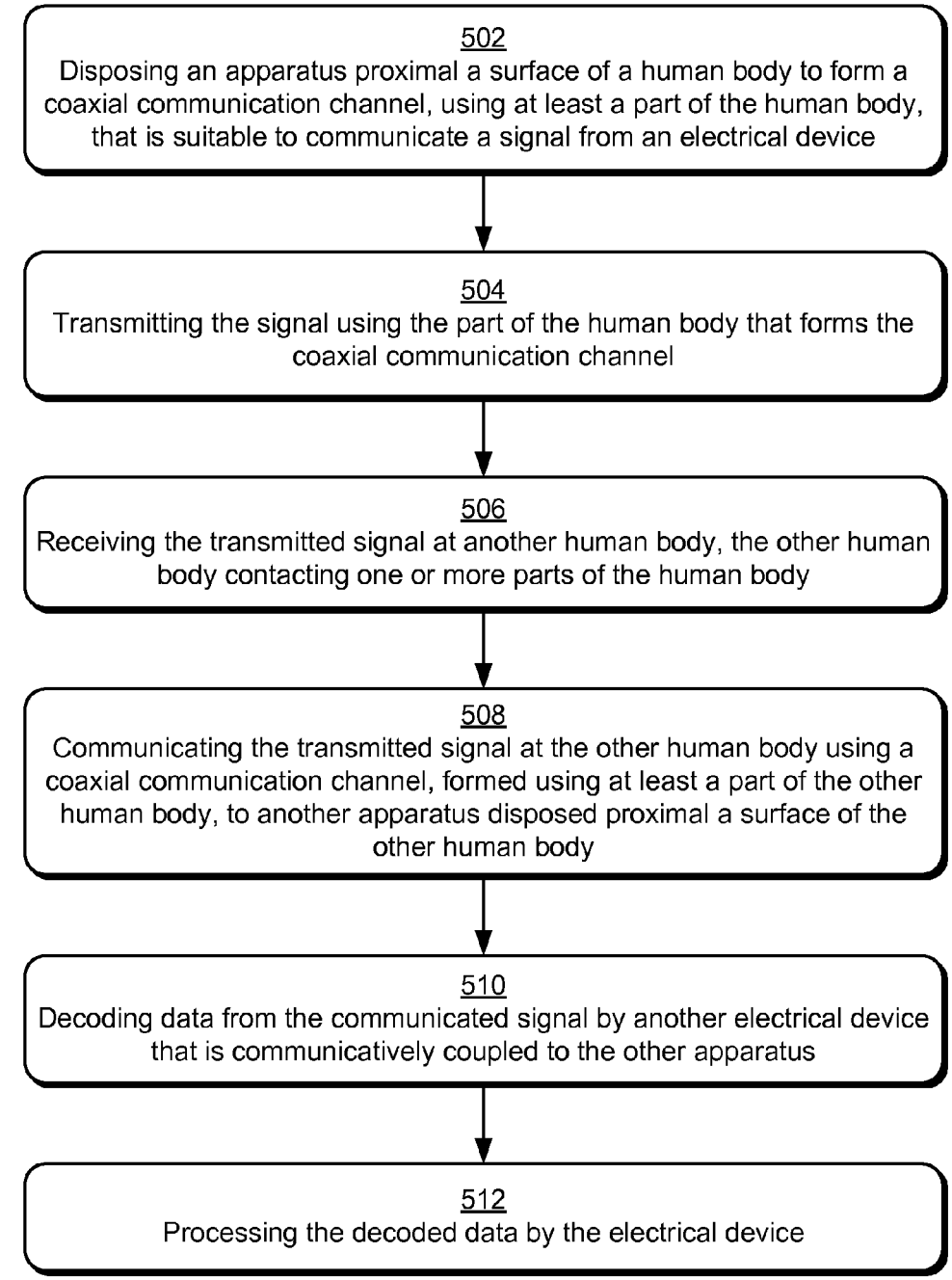
FIG. 5 is a flow diagram depicting a procedure in an example implementation in which communication between two electrical devices is performed by communicating a signal through a communication channel formed using two human bodies.

FIG. 5 depicts a procedure 500 in an example implementation in which communication between two electrical devices is performed by communicating a signal through a communication channel formed using two human bodies. An apparatus is disposed proximal to a surface of a human body to form a coaxial communication channel, using at least a part of the human body that is suitable to communicate a signal from an electrical device (block 502). Apparatus 102, for instance, may be disposed against a user's arm or other parts of the user's body, such as in a pocket of the user. The apparatus 102, as previously described, may be configured to form a coaxial communication channel, such as by disposing a signal conductor 202 between a ground layer 204 and the user's arm 104 such that a signal is transmitted from the signal conductor 202 to the user's arm 104 for transmission as a guided wave through the user's arm 104.

The signal is transmitted using the part of the human body that forms the coaxial communication channel (block 504). The signal, for instance, may be communicated from the electrical device 106 to the signal conductor 202, which may then be "picked up" by skin 306 of the user's arm 104 and transmitted as a guided wave as previously described.

The transmitted signal is received at another human body, the other human body contacting one or more parts of the human body (block 506). A user wearing the apparatus 102, for instance, may shake hands or otherwise contact another user. Accordingly, the other user may then receive the signal transmitted by the apparatus 102 through the user's arm 104.

The transmitted signal is communicated at the other human body using a coaxial communication channel, formed using at least a part of the other human body, to another apparatus disposed proximal to a surface of the other human body (block 508). Continuing with the previous example, the other user may also be wearing an apparatus 406 similar to the apparatus 102 worn by the user, but in this instance is configured to detect a signal transmitted by the body 404 of the other user.

Data from the communicated signal is decoded by another electrical device that is communicatively coupled to the other apparatus (block 510). The electrical device 112, for instance, may be configured to extract data from the signal transmitted by the electrical device 106 to the apparatus 102 for communication as a guided wave through the user's arm 104 to a body 404 of the other user and detected by the other apparatus 406. The decoded data is then processed by the other electrical device (block 512), such as to detect and verify credentials, process transaction information, receive contact information, receive a message, and a variety of other types of data as previously described.

FIG. 6 depicts a procedure 600 in an example implementation in which communication of first and second signals is performed to support communication that is both bounded and unbounded by a biological channel. A first signal is communicated by an apparatus as a guided wave to transmit data as bounded to a biological channel (block 602). A second signal is communicated by the apparatus as a wave to transmit data as unbounded by the biological channel (block 604).

For example, the first signal may be communicated at a frequency that is sufficiently low such that leakage of the signal is minimized. The second signal may be communicated at a higher frequency than the first signal, such as at a frequency that permits a desired range of communication, such as to communicate via one or more wireless communication standards such as IEEE 802.11, Bluetooth, and so on. In one or more implementations, this communication may be performed simultaneously by the apparatus. A variety of other examples are also contemplated.

Example Device

Figure 7:
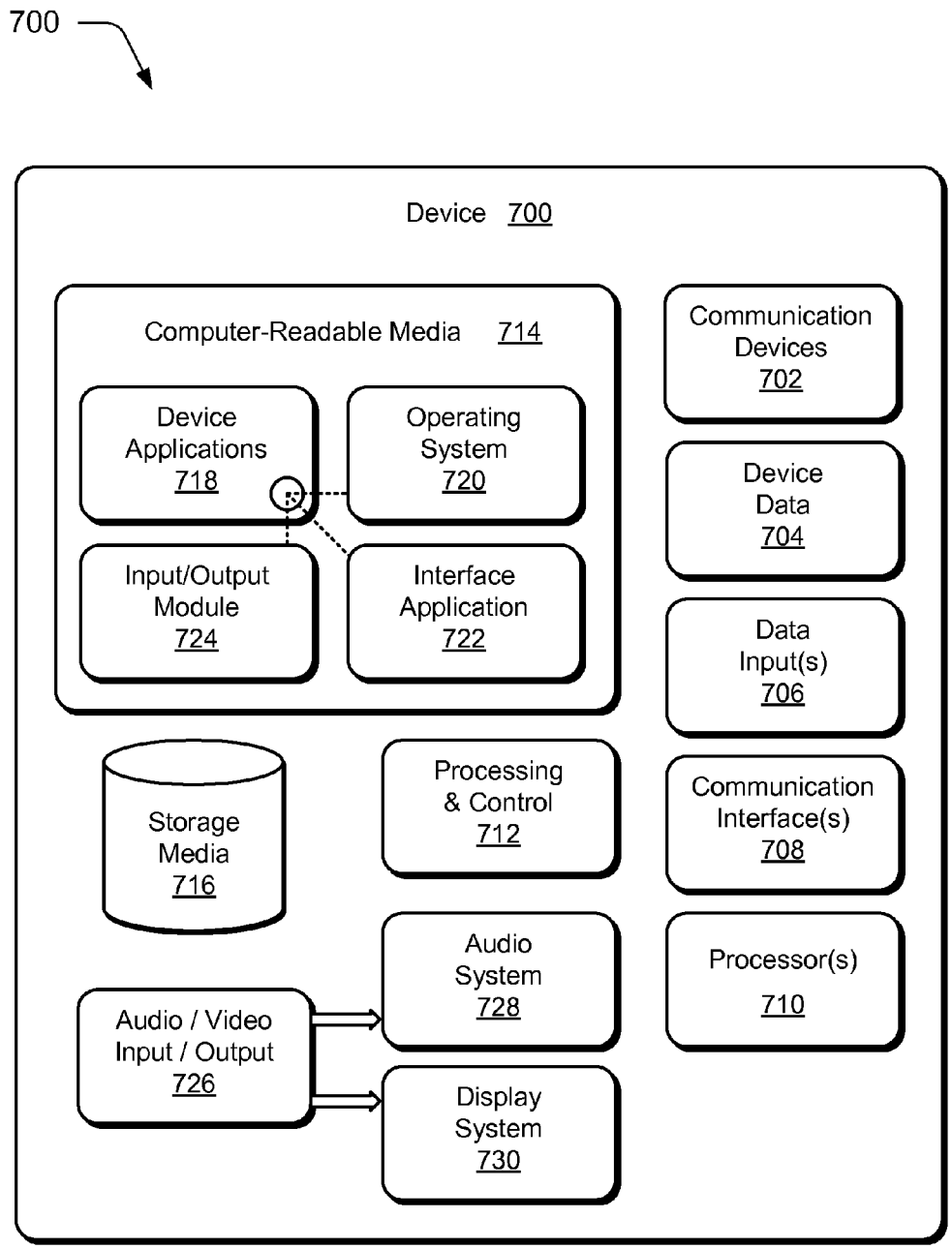
FIG. 7 illustrates various components of an example device that can be implemented in various embodiments as any type of a mobile device to implement embodiments of devices, features, and systems for mobile communications.

FIG. 7 illustrates various components of an example device 700 that can be implemented as any type of computing device as described with reference to FIGS. 1, 2, and to implement embodiments of the techniques described herein. Device 700 includes communication devices 702 that enable wired and/or wireless communication of device data 704 (e.g., received data, data that is being received, data scheduled for broadcast, data packets of the data, etc.). The device data 704 or other device content can include configuration settings of the device, media content stored on the device, and/or information associated with a user of the device. Media content stored on device 700 can include any type of audio, video, and/or image data. Device 700 includes one or more data inputs 706 via which any type of data, media content, and/or inputs can be received, such as user-selectable inputs, messages, music, television media content, recorded video content, and any other type of audio, video, and/or image data received from any content and/or data source.

Device 700 also includes communication interfaces 708 that can be implemented as any one or more of a serial and/or parallel interface, a wireless interface, any type of network interface, a modem, and as any other type of communication interface. The communication interfaces 708 provide a connection and/or communication links between device 700 and a communication network by which other electronic, computing, and communication devices communicate data with device 700.

Device 700 includes one or more processors 710 (e.g., any of microprocessors, controllers, and the like) which process various computer-executable instructions to control the operation of device 700 and to implement embodiments of the techniques described herein. Alternatively or in addition, device 700 can be implemented with any one or combination of hardware, firmware, or fixed logic circuitry that is implemented in connection with processing and control circuits which are generally identified at 712. Although not shown, device 700 can include a system bus or data transfer system that couples the various components within the device. A system bus can include any one or combination of different bus structures, such as a memory bus or memory controller, a peripheral bus, a universal serial bus, and/or a processor or local bus that utilizes any of a variety of bus architectures.

Device 700 also includes computer-readable media 714, such as one or more memory components, examples of which include random access memory (RAM), non-volatile memory (e.g., any one or more of a read-only memory (ROM), flash memory, EPROM, EEPROM, etc.), and a disk storage device. A disk storage device may be implemented as any type of magnetic or optical storage device, such as a hard disk drive, a recordable and/or rewriteable compact disc (CD), any type of a digital versatile disc (DVD), and the like. Device 700 can also include a mass storage media device 716.

Computer-readable media 714 provides data storage mechanisms to store the device data 704, as well as various device applications 718 and any other types of information and/or data related to operational aspects of device 700. For example, an operating system 720 can be maintained as a computer application with the computer-readable media 714 and executed on processors 710. The device applications 718 can include a device manager (e.g., a control application, software application, signal processing and control module, code that is native to a particular device, a hardware abstraction layer for a particular device, etc.). The device applications 718 also include any system components or modules to implement embodiments of the techniques described herein. In this example, the device applications 718 include an interface application 722 and an input/output module 724 that are shown as software modules and/or computer applications. The input/output module 724 is representative of software that is used to provide an interface with a device configured to capture inputs, such as a touchscreen, track pad, camera, microphone, and so on. Alternatively or in addition, the interface application 722 and the input/output module 724 can be implemented as hardware, software, firmware, or any combination thereof. Additionally, the input/output module 724 may be configured to support multiple input devices, such as separate devices to capture visual and audio inputs, respectively.

Device 700 also includes an audio and/or video input-output system 726 that provides audio data to an audio system 728 and/or provides video data to a display system 730. The audio system 728 and/or the display system 730 can include any devices that process, display, and/or otherwise render audio, video, and image data. Video signals and audio signals can be communicated from device 700 to an audio device and/or to a display device via an RF (radio frequency) link, S-video link, composite video link, component video link, DVI (digital video interface), analog audio connection, or other similar communication link. In an embodiment, the audio system 728 and/or the display system 730 are implemented as external components to device 700. Alternatively, the audio system 728 and/or the display system 730 are implemented as integrated components of example device 700.

Conclusion

Although the invention has been described in language specific to structural features and/or methodological acts, it is to be understood that the invention defined in the appended claims is not necessarily limited to the specific features or acts described. Rather, the specific features and acts are disclosed as example forms of implementing the claimed invention.

What is claimed is:

1. An apparatus comprising:
a signal conductor capable of radiating signals in one or more distinct bands having a side that is configured to be disposed proximal to a surface of part of a first biological entity to use as a transmission channel to transmit a signal received by the signal conductor from a first electrical device, the signal transmitted as a guided wave substantially undetectable outside of the first biological entity; and
a ground layer arranged coaxially next to the signal conductor and configured to be disposed on an opposing side of the signal conductor from the side of the signal conductor that is configured to be disposed against the surface of the part of the first biological entity, the coaxial configuration of the ground layer in relation to the signal conductor causing formation of a coaxial channel using the part of the first biological entity to serve as the transmission channel, wherein part of the first biological entity and part of a second biological entity in contact with one another communicate purchase credentials over the transmission channel between the first device and a second device of another apparatus as a result of the contact between the parts of the first and second biological entities, and wherein the other apparatus comprises another signal conductor and the signal conductors of the first and second devices are disposed proximal to surfaces of the parts of the first and second biological entities.

2. An apparatus as described in claim 1, wherein the first and second biological entities are mammals.

3. An apparatus as described in claim 1, wherein the signal conductor and the ground layer of the first electrical device are separated by an insulator.

4. An apparatus as described in claim 1, wherein the signal is configured for transmission through the parts of the first and second biological entities as a guided-wave, thereby reducing leakage of the signal.

5. An apparatus as described in claim 1, wherein a first signal is configured for transmission through the parts of the first and second biological entities as a guided-wave and a second signal is configured for transmission through space as a separate transmission in the form of space-waves simultaneously with the first signal.

6. An apparatus as described in claim 1, wherein the signal conductor is a sole conductor used to communicate via the first biological entity by the apparatus.

7. An apparatus as described in claim 1, wherein the data includes protocols to communicate in compliance with one or more wireless standards.

8. A method comprising:
communicating a first signal at a first signal frequency by a first apparatus as a guided wave to transmit data as bounded to a biological channel between first and second biological entities in contact with one another to a second apparatus, the biological channel and the first apparatus arranged coaxially to form a coaxial communication channel, the transmitted data from the first signal substantially undetectable outside of the first and second biological entities; and
communicating a second signal at a second signal frequency by the first apparatus as a wave to transmit data as unbounded by the biological channel between first and second biological entities, the transmitted data from the second signal substantially detectable outside of the first and second biological entities.

9. A method as described in claim 8, wherein the communicating of the first and second signals is performed simultaneously.

10. A method as described in claim 8, wherein the communication of the first and second signals is performed at different frequencies such that the first signal is bounded to the biological channel and the second signal is unbounded by the biological channel.

11. A method as described in claim 8, wherein the first signal frequency is a signal at 400 MHz and second signal frequency is a signal at 1.5 GHz.

12. A system comprising:
a first electrical device configured to generate a signal;
a first apparatus comprising a signal conductor capable of radiating signals in one or more distinct bands having a side that is configured to be disposed proximal to a surface of a first biological entity to use at least a part of the first biological entity as a transmission channel to transmit a signal received by the signal conductor from the first electrical device, and a ground layer arranged coaxially next to the signal conductor and configured to be disposed on an opposing side of the signal conductor from the side of the signal conductor that is configured to be disposed against the surface of the first biological entity, the coaxial configuration of the ground layer in relation to the signal conductor causes formation of a coaxial channel using the part of the first biological entity to serve as the transmission channel, and security or bandwidth of the signal adjusted through adjustments to the signal conductor;

a second electrical device configured to generate a signal; and a second apparatus comprising another signal conductor capable of radiating signals in one or more distinct bands having a side that is configured to be disposed proximal to a surface of a second biological entity to use at least a part of the second biological entity as a transmission channel to transmit a signal received by the signal conductor from the second electrical device, and a ground layer arranged coaxially next to the signal conductor and configured to be disposed on an opposing side of the signal conductor from the side of the signal conductor that is configured to be disposed against the surface of the second biological entity, the coaxial configuration of the ground layer in relation to the signal conductor causes formation of a coaxial channel using the part of the second biological entity to also serve as the transmission channel, and security or bandwidth of the signal adjusted through adjustments to the signal conductor, wherein part of the first biological entity and part of the second biological entity in contact with one another communicate purchase credentials over the transmission channel between the first and second devices as a result of the contact between the parts of the first and second biological entities.

13. A system as described in claim 12, wherein the signal conductor and the ground layer of each of the first and second electrical devices are separated by an insulator.

14. A system as described in claim 12, wherein each signal conductor is a sole conductor used to communicate via the first and second biological entities.

* * * * *